United States Patent
Landgraf

(10) Patent No.: US 7,511,268 B2
(45) Date of Patent: Mar. 31, 2009

(54) ION MOBILITY SPECTROMETER AND ITS METHOD OF OPERATION

(75) Inventor: Jürgen Landgraf, Gutenberg (DE)

(73) Assignee: Bruker Daltonik, GmbH, Bremen (DE)

( * ) Notice: Subject to any disclaimer, the term of this patent is extended or adjusted under 35 U.S.C. 154(b) by 455 days.

(21) Appl. No.: 11/340,421

(22) Filed: Jan. 26, 2006

(65) Prior Publication Data

US 2006/0192103 A1    Aug. 31, 2006

(30) Foreign Application Priority Data

Jan. 31, 2005    (DE) .................. 10 2005 004 325

(51) Int. Cl.
*B01D 59/44*    (2006.01)

(52) U.S. Cl. .............. 250/288; 250/281; 250/428; 250/430; 250/431; 422/83; 436/153

(58) Field of Classification Search ............. 250/281, 250/287, 288, 423 R, 428, 430, 431; 422/83; 436/153
See application file for complete search history.

(56) References Cited

U.S. PATENT DOCUMENTS

| | | | |
|---|---|---|---|
| 3,699,333 A | 10/1972 | Cohen et al. | |
| 4,311,669 A * | 1/1982 | Spangler | 422/98 |
| 4,777,363 A | 10/1988 | Eiceman et al. | |
| 5,109,691 A * | 5/1992 | Corrigan et al. | 73/23.36 |
| 5,420,424 A * | 5/1995 | Carnahan et al. | 250/287 |
| 5,723,861 A * | 3/1998 | Carnahan et al. | 250/287 |
| 5,736,739 A * | 4/1998 | Uber et al. | 250/287 |
| 5,811,059 A | 9/1998 | Genovese et al. | |
| 5,968,837 A * | 10/1999 | Doring et al. | 436/173 |
| 6,803,567 B2 * | 10/2004 | Leonhardt et al. | 250/288 |
| 7,211,791 B2 * | 5/2007 | Miller et al. | 250/286 |
| 2002/0016004 A1 * | 2/2002 | Nguyen et al. | 436/39 |
| 2003/0036272 A1 * | 2/2003 | Shamouilian et al. | 438/691 |
| 2005/0085740 A1 * | 4/2005 | Davis et al. | 600/532 |
| 2005/0139762 A1 * | 6/2005 | Miller | 250/282 |
| 2006/0102844 A1 * | 5/2006 | Sauer et al. | 250/339.13 |
| 2006/0249673 A1 * | 11/2006 | Breach et al. | 250/292 |

FOREIGN PATENT DOCUMENTS

| | | |
|---|---|---|
| DE | 195 02 674 C1 | 9/1996 |
| DE | 199 38 392 A1 | 2/2001 |
| DE | 102 54 960 A1 | 6/2004 |
| DE | 103 10 394 A1 | 9/2004 |
| EP | 0774663 A1 | 5/1997 |
| WO | WO 93/06476 A1 | 4/1993 |
| WO | WO 97/38302 A1 | 10/1997 |

\* cited by examiner

*Primary Examiner*—David A. Vanore
*Assistant Examiner*—Michael J Logie
(74) *Attorney, Agent, or Firm*—Law Offices of Paul E. Kudirka

(57) ABSTRACT

The invention relates to an ion mobility spectrometer in which a measuring tube, a filter and a transport device are connected to form a circulatory gas system, with a gas inlet which introduces ambient gas for analysis into the measuring tube of the ion mobility spectrometer. The invention involves connecting the measuring tube with the ambient gas by means of a dosing channel and connecting the circulatory gas system with the ambient gas by means of an outlet channel. The outlet channel joins the circulatory gas system between the high-pressure side of the transport device and the measuring tube, so that ambient gas for analysis is introduced into the measuring tube via the dosing channel while, at the same time, gas flows out of the circulatory gas system via the outlet channel without further transport devices being required.

12 Claims, 5 Drawing Sheets

ION MOBILITY SPECTROMETER AND ITS METHOD OF OPERATION

FIELD OF THE INVENTION

The invention relates to an ion mobility spectrometer in which a measuring tube, a filter and a transport device are connected to form a circulatory gas system, with a gas inlet which introduces ambient gas for analysis into the measuring tube of the ion mobility spectrometer.

BACKGROUND OF THE INVENTION

In a wide range of applications, gaseous substances are analyzed and continuously monitored, for example in environmental analysis, in the control of chemical processes, and for detecting chemical warfare agents or explosives in the civil and military fields.

Ion mobility spectrometry (IMS) is a method introduced from the 1970s onward for the highly sensitive detection of substances at low concentrations in air or other gases. An ion mobility spectrometer is operated at ambient pressure and is distinguished by its comparatively compact design, which can be realized with a technically simple set-up, making ion mobility spectrometers particularly suitable as portable and mobile gas monitors and warning devices.

Ion mobility spectrometry has been elucidated in U.S. Pat. No. 3,699,333 (Cohen et al.) and U.S. Pat. No. 4,777,363 (Eiceman), for example.

The measuring tube of the most commonly used time-of-flight type of ion mobility spectrometer comprises a reaction chamber, in which the substances to be analyzed are partially ionized, and a drift chamber in which the ions generated are separated according to their mobility in a drift gas. The two chambers are separated by an electric gating grid. In the reaction chamber, radioactive materials such as $^{63}$Nickel are usually used for the primary ionization of gas molecules, but other ionization methods are also possible, for example a corona discharge. The ionization of the substances to be analyzed typically takes place only in secondary reactions. The ions generated in the reaction chamber are admitted into the drift chamber by opening the electric gating grid for a short time. There the ions move through the drift gas in an axial electric field to the other end of the drift chamber, where they are measured as an ion current at a collecting electrode. The ions are temporally separated in the drift chamber because their speed in the drift gas is substance-specific. The time delays of the ion current measured at the collecting electrode with reference to the opening of the electric gating grid are used to determine the substance-specific drift times as a measure of ion mobility. When parameters such as the gas temperature and gas pressure are taken into account, the drift times are characteristic of the respective substances. In the measuring tube, the gas is guided in such a way that the gaseous substances to be analyzed preferably only reach the reaction chamber, and the cleaned drift gas flows through the drift chamber in the opposite direction to the ion drift.

In other types of ion mobility spectrometer, for example the filter types (FAIMS: "Field Asymmetric Ion Mobility Spectrometer") or the multi-electrode types (aspiration type), the ions move in electric fields aligned radially or transversely to the longitudinal axis of the drift chamber. A drift gas which flows through the drift chamber at right angles to the electric fields transports the ions longitudinally through the drift chamber.

In order to achieve reproducible results, particularly with an ion mobility spectrometer of the time-of-flight type, the drift gas, in which the ions move, must be continuously cleaned and freed of moisture, which is carried into the ion mobility spectrometer by the sample gas introduced.

An alternative gas exchange by feeding from supply tanks or external gas processing units is primarily suitable for stationary operation. In most mobile ion mobility spectrometers the drift gas is guided in a closed loop circulatory gas system through a filter with the help of a transport device such as a gas pump or a fan. This removes the moisture from the gas in the circulatory gas system and cleans it before it is conveyed back again to the measuring tube of the ion mobility spectrometer. Ion mobility spectrometers of the filter and multi-electrode type typically have no circulatory gas system, and until now have been mainly flushed directly with the sample gas introduced. However, they often exhibit a saturation effect even at substance concentrations relevant to use in the field, which limits their practical range of application.

With an ion mobility spectrometer with a circulatory gas system, the defined introduction of sample gas for analysis out of ambient gas that is not at a higher pressure is often a task which is beset with problems. In the case of a mobile ion mobility spectrometer, the sample gas to be analyzed is preferably introduced into the circulatory gas system either upstream of, or in the area of, the measuring tube, where it mixes with the gas of the circulatory gas system. The following technical variants have been elucidated:

a) permeation of the gaseous substances to be detected through a membrane that is semipermeable to these substances and is flushed from outside with sample gas (U.S. Pat. No. 4,311,669 by Spangler et al.), b) introduction of gas loops or vessels charged with sample gas into the circulatory gas system with the help of valve actuations (DE Patent 195 02 674 by Leonhardt et al.), c) aspiration of the sample gas with the help of a vacuum pump connected to a valve actuation (U.S. Pat. No. 5,811,059 by Genevese et al.), d) periodic aspiration of sample gas through a narrow aperture with the help of low-pressure pulses generated by a pump membrane (WO Patent 93/06476 by Bradshaw) and e) feeding in sample gas by means of a perforated disk made of gas-impermeable material, arranged between the ambient gas and the measuring tube of the ion mobility spectrometer, the disk being actively set in oscillation to generate periodic pressure differences (EP Patent 0 774 663 by Grossniklaus et al.).

Experience has shown that using a semipermeable membrane, as done by Spangler et. al, for example, requires electrical heating in order to minimize delay and accumulation effects in the membrane material. The energy required for heating reduces the operating time, especially in the case of battery-operated mobile gas monitors, without completely eliminating the accumulation effects and the delayed reaction to variations in the external concentration. Moreover, the manufacture and assembly of the thin semipermeable membranes is complex and expensive. Furthermore, membranes of this type are mechanically sensitive because of the small layer thicknesses which are required.

The technical variants b) to e) are direct inlet systems which introduce the sample gas to be analyzed directly into the circulatory gas system, and thus avoid significant disadvantages of the membrane systems. One disadvantage of the direct inlet systems used until now, however, is that they additionally require special transport devices or valves plus the associated actuating components (such as motors, solenoids or piezoelectric actuators) to aspirate sample gas either continuously or in pulses. This makes manufacturing complex and costly, and also involves additional energy consumption, which in turn reduces the operating time of a set of batteries in battery-operated instruments, or forces one to use larger and heavier batteries, making the instruments less compact. In variant a), in addition to the transport device in the circulatory gas system, a further transport device is used to flush the semipermeable membrane.

In direct inlet systems without a membrane, the accumulation of low-volatility substances in the inlet region and on the inner wall of the measuring tube of the ion mobility spectrometer still occurs, to a lesser degree, as a result of condensation, adsorption and solubility effects. Consequently, these systems are also saturated for a certain time after a large amount of substance has been admitted, and are thus no longer ready to measure for a certain time. This is particularly problematic in the set-up of valves described in DE Patent 195 02 674 (Leonhardt et al.) since, in this case, the sample gas to be analyzed flows through further valves upstream of the gas analyzer. The method usually used in stationary instruments, and especially in membrane systems, to minimize these accumulation effects is to heat the inlet region, but this is only possible to a limited extent in mobile instruments because of the energy required. To accelerate the desorption of the accumulated substances, the only other possibility remaining is therefore the specific flushing of the measuring tube and the inlet region with a cleaned gas stream, which is directed toward the introduced sample gas in the inlet region. Gas aspirated from outside, which is cleaned in a special back flush filter, is used for the so-called back flushing. The systems used up to now require further components (e.g. valves and pumps), however, which again complicate manufacture and create additional energy consumption.

A further disadvantage of the direct inlet systems from the WO patent 93/06476 (Bradshaw) and the EP patent (Grossniklaus et al.) is the fact that the gas streams directed inward and outward, which are caused by the periodic high- and low-pressure phases of the pump membrane or oscillating perforated disk, only transport very small amounts of gas. The volume of the dosing channel is kept as small as possible here so that, during a low-pressure phase, sufficient sample gas reaches the inside of the measuring tube of the ion mobility spectrometer.

SUMMARY OF THE INVENTION

The present invention provides an ion mobility spectrometer in which a measuring tube, a filter and a transport device are connected to form a circulatory gas system, with a gas inlet which introduces ambient gas for analysis into the measuring tube of the ion mobility spectrometer without using additional transport devices. The invention involves connecting the measuring tube with the ambient gas by means of a dosing channel and connecting the circulatory gas system with the ambient gas by means of an outlet channel. The outlet channel joins the circulatory gas system between the high-pressure side of the transport device and the measuring tube, so that ambient gas for analysis is introduced into the measuring tube via the dosing channel while, at the same time, gas flows out of the circulatory gas system via the outlet channel without further transport devices being required.

The present invention is based on the discovery that it is very easy to introduce ambient gas for analysis into the measuring tube of an ion mobility spectrometer with a circulatory gas system if both the measuring tube and the circulatory gas system are connected with the ambient gas, via a dosing channel and an outlet channel respectively, wherein the outlet channel is integrated into the circulatory gas system between the high-pressure side of the transport device and the measuring tube. Since the pressures at the points where the two channels join the circulatory gas system are different, ambient gas (sample gas) for analysis is introduced into the measuring tube via the dosing channel, and gas flows out of the circulatory gas system at the same time via the outlet channel. It is also advantageous that contamination of the sample gas by the substances accumulated in the dosing channel is reduced because the dosing channel directly joins the measuring tube of the ion mobility spectrometer, and hence the sample gas does not come into contact with accumulating components, such as valves or transport devices. According to the invention, more than one channel can be used as the dosing and outlet channel respectively. Surprisingly, with this new type of direct inlet system the transport device of the circulatory gas system is sufficient to introduce the sample gas directly into the measuring tube.

BRIEF DESCRIPTION OF THE DRAWINGS

The above and further advantages of the invention may be better understood by referring to the following description in conjunction with the accompanying drawings in which.

DETAILED DESCRIPTION

Figure 1:
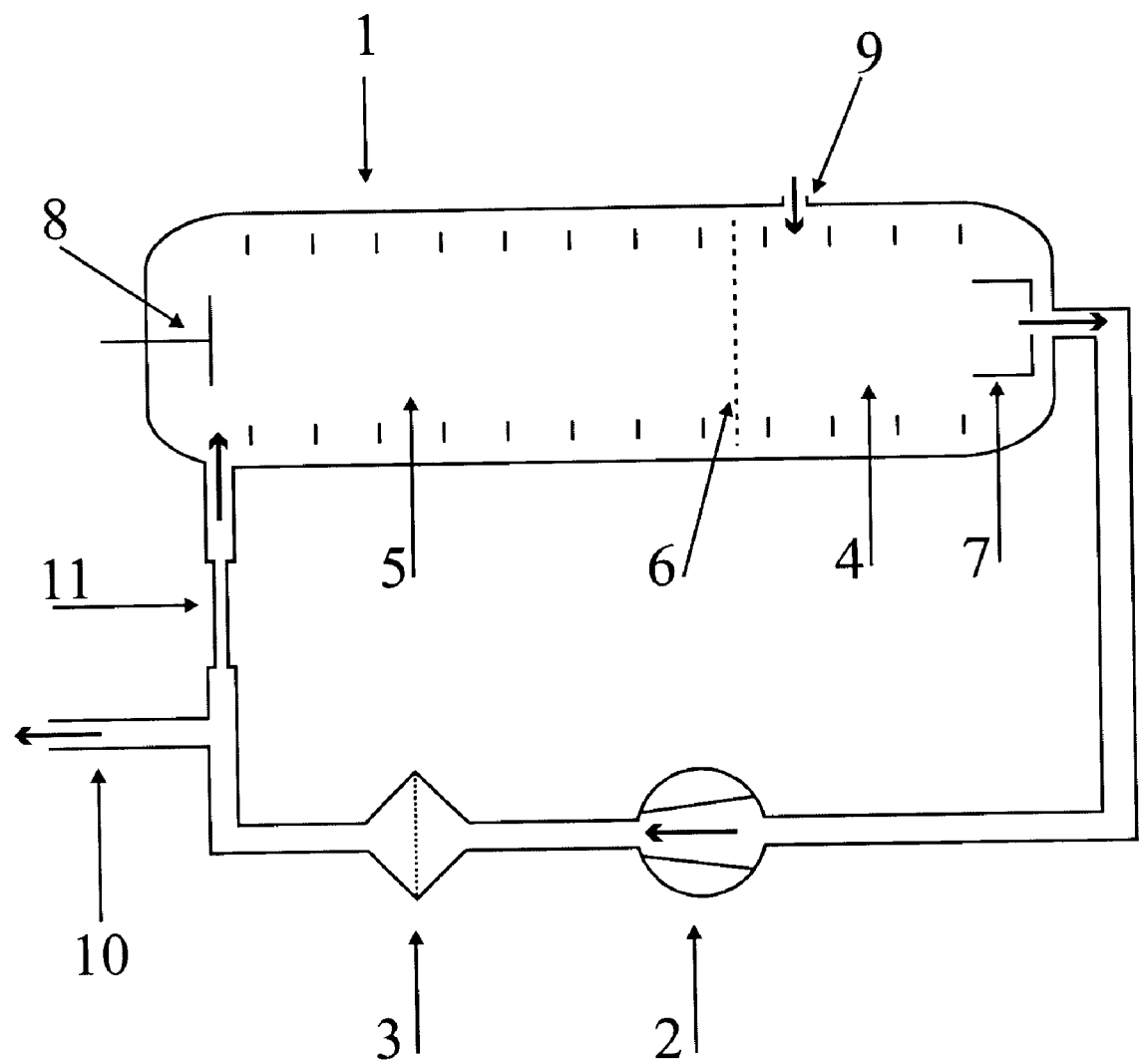
FIG. 1 shows an ion mobility spectrometer with a dosing channel and an outlet channel.

FIG. 1 shows a first preferred embodiment of an ion mobility spectrometer according to the invention with a measuring tube (1) of the time-of-flight type. The measuring tube (1) of known design comprises a reaction chamber (4) and a drift chamber (5) separated by a gating grid (6). The primary ionization of gas molecules takes place in close proximity to the ionization source (7), which contains a radioactive beta emitter ($^{63}$Nickel). The gas ions generated are drawn by an electric field toward the gating grid (6). Typically, the substances to be analyzed, which reach the reaction chamber (4) with the sample gas, are ionized only after a cascade of reactions. Ions are admitted into the drift chamber (5) by opening the electric gating grid for a short time; there they move in an axial electric field to the collecting electrode (8). A time-dependent current is measured at the collecting electrode (8) because the mobility of the ions is substance-dependent.

The ion mobility spectrometer in FIG. 1 comprises a circulatory gas system in which a gas pump (2) circulates the gas in the circulatory gas system through the measuring tube (1) and the filter (3). The gas is sucked off near the ionization source (7), and it flows back into the drift chamber (5) at the collecting electrode (8). The ion drift to the collecting electrode (8) is thus in the opposite direction to the gas stream. In the filter (3), the gas is cleaned of the substances to be analyzed and freed of moisture. The moisture is kept constant in the measuring tube (1) and amounts to less than 100 ppm (parts per million), preferably around 10 ppm.

In this embodiment, the dosing channel (9) consists of an aperture or several apertures in the reaction chamber (4) of the measuring tube (1). The outlet channel (10) is shaped as a capillary, which is integrated into the circulatory gas system between the filter (3) and the flow resistor (11). Because of the flow resistances in the circulatory gas system, especially that of the flow resistor (11), and because of the flow resistances of the dosing channel (9) and outlet channel (10), there is a pressure difference between the points at which the two channels join the circulatory gas system, which causes the sample gas to be introduced into the measuring tube (1) via the dosing channel (9) and gas to flow out via the outlet channel (10). The sample gas passes via the dosing channel (9) directly into the reaction chamber (4) and does not come into contact with other components, thus considerably reducing accumulation effects. The substances to be analyzed are ionized in secondary ionization processes in the reaction chamber (4).

The flow rate of the sample gas is determined by the pressure difference between the two channels (9) and (10) and also by the flow resistances of the two channels. The ratio between the flow rate of the sample gas and the flow rate in the circulatory gas system is given by the quotient of the flow resistance of the section of the circulatory gas system between the points, where the dosing channel (9) and outlet channel (10) join the circulatory gas system, and the sum of the flow resistances of these two channels. In this case, the section of the circulatory gas system is understood to be the section in the direction of the flow. An appropriate choice of pipe cross-sections and lengths, or the introduction of additional nozzles, orifice plates or other restrictions, makes it possible to adjust the mixing ratio between the sample gas and the gas in the circulatory gas system over a wide range. Mixing ratios of between 1:20 and 1:1000 have proven to be particularly suitable. The flow rate of the sample gas is typically between 1 and 20 milliliters per minute, and the flow rate in the circulatory gas system between 0.1 and 2 liters per minute.

The flow resistances of the dosing channel (9) and outlet channel (10), and in particular the flow resistor (11), can be changed when the ion mobility spectrometer is in operation, preferably by electrically controlled actuators or switches, so that the flow rate of the sample gas and the mixing ratio can be varied. The flow resistances can be varied continuously or stepwise, depending on the actuators or switches and their controls. The control software of the ion mobility spectrometer can compare the measuring signals with specified limit values and, with the help of the electrically controlled actuators or switches, adapt the flow rate of the sample gas to the concentration of the substances to be analyzed. This type of control system increases the dynamic range of measurement of the ion mobility spectrometer and protects the ion mobility spectrometer against too high concentrations. The delay and accumulation effects at high concentrations are reduced and hence the time required to restore the measurement readiness is shortened.

A further advantage is that the mixing ratio between the sample gas introduced and the gas in the circuit is not dependent on the delivery capacity of the gas pump (2), which can vary as the temperature or voltage varies, or as it ages. There is therefore no need to stabilize or readjust the delivery capacity of the gas pump (2). The gas pump (2) circulates the gas through the circulatory gas system and introduces sample gas into the measuring tube (1) at the same time. Apart from the gas pump (2), no further transport devices, such as additional gas pumps, fans, oscillating perforated disks or pump membranes, are required.

In most applications, the ambient gas is the ambient air. The continuous monitoring of other gases in open or closed reservoirs is also possible, however. When analyzing flowing media, for example in a gas pipe, care must be taken that all channels connecting the ambient gas with the circulatory gas system of the gas monitor are located closely together in the flowing medium and preferably all present the same angle to the flow in order to avoid additional flow pressures.

The dosing channel (9) and the outlet channel (10) are constantly open in operation. The introduction of the sample gas can be very simply controlled by opening and closing the outlet channel. When the ion mobility spectrometer is not in operation, a locking cap is fitted to the two channels (9) and (10), cutting them off from the outside air, to prevent contamination and blockages. The locking cap can also connect the two channels so that the dosing channel (9) and the outlet channel (10) are flushed with filtered air and hence, most importantly, the dosing channel (9) is cleaned of accumulated substances. The accumulated substances are removed from the circulating gas in the filter (3). Since no outside air gets into the instrument in this process, the filter (3) is not additionally loaded by the entry of moisture; this produces a stand-by mode with a self-cleaning function. It is particularly important to clean the dosing channel (9) if it is configured not as simple apertures in the measuring tube (1) but as capillary.

Figure 2:
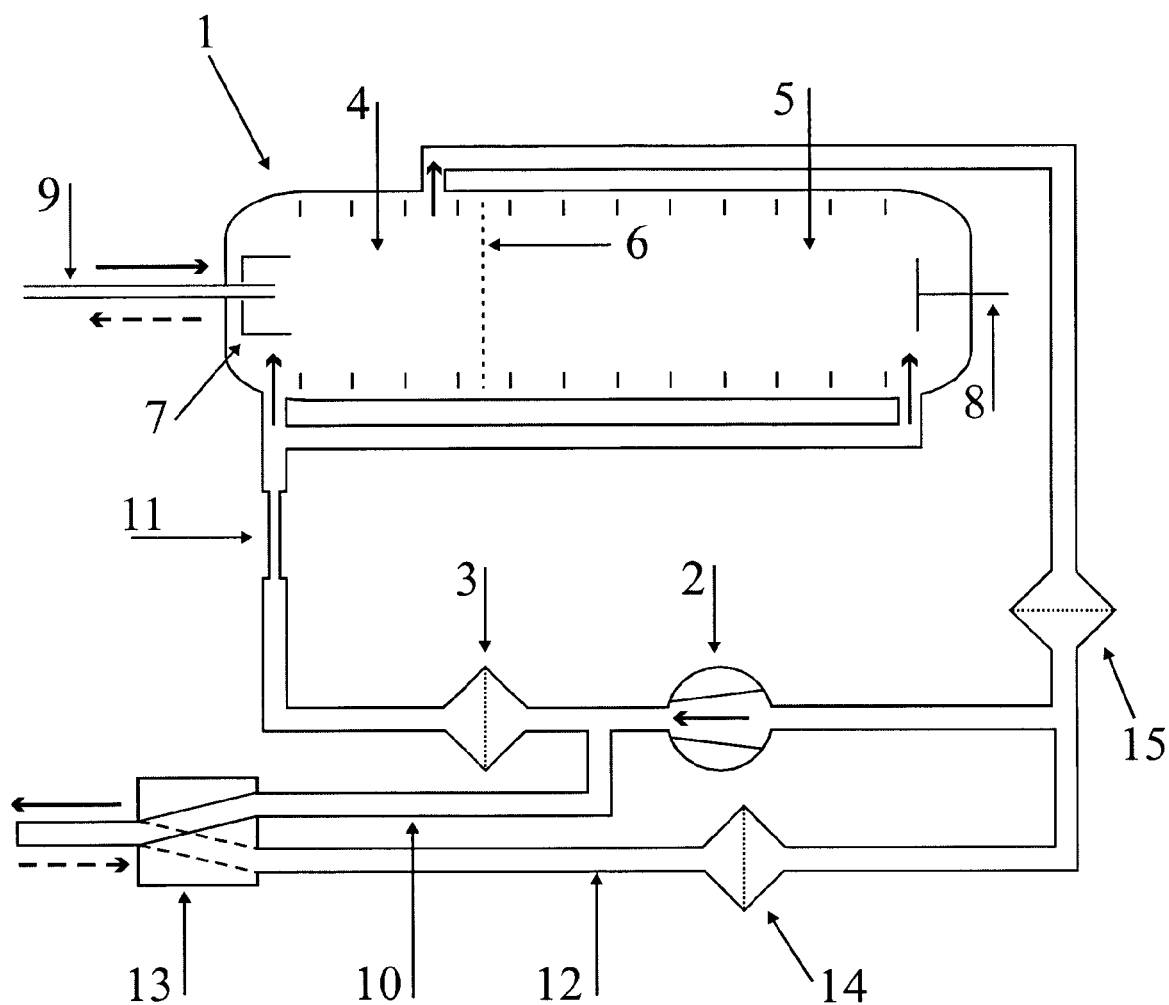
FIG. 2 shows an ion mobility spectrometer with a dosing channel, an outlet channel and a flushing channel. A valve permits switching between "dosing mode" and "back flush mode".

FIG. 2 shows a second preferred embodiment of an ion mobility spectrometer. Compared to FIG. 1, this embodiment comprises an additional flushing channel (12), which joins the circulatory gas system on the low-pressure side of the gas pump (2). The outlet channel (10) is integrated into the circulatory gas system between the high-pressure side of the gas pump (2) and the filter (3). The changeover valve (13) enables either the outlet channel (10) or the flushing channel (12) to be connected with the ambient gas. The ion mobility spectrometer comprises a circulatory gas system in which the gas pump (2) circulates the gas in the circulatory gas system through the measuring tube (1) and the two filters (3) and (15). The gas is sucked off from the reaction chamber (4) near the gating grid (6), and flows back into the reaction chamber (4) and drift chamber (5) at both ends of the measuring tube (1). As in the preceding embodiment, the gas pump (2) here is again the sole transport device of the ion mobility spectrometer.

The dosing channel (9) here is configured as a thin capillary which directly joins the reaction chamber (4). Because of the flow resistor (11) and the filter (3), the pressure at the point where the dosing channel (9) joins the circuit is lower than the pressure at the point where the outlet channel (10) joins it. When the outlet channel (10) is open ("dosing mode"), this pressure difference results in the ambient gas (sample gas) for analysis being introduced into the circulatory gas system via the dosing channel (9) and gas from the circulatory gas system flowing out via the outlet channel (10).

Advantageously, the sample gas does not come into contact with other components, such as valves or other transport devices. To reduce the accumulation of the substances in the dosing channel (9) even further, it is typical to use deactivated (inert) quartz glass capillaries, which also have a small diameter of around 0.25 millimeters and a length of a few centimeters. These capillaries are also used, for example, in gas chromatography (GC) as transfer capillaries. Using a capillary as a dosing channel (9) facilitates spatial separation of the ion mobility spectrometer from the ambient gas.

If the flushing channel (12) is connected with the ambient gas via the changeover valve (13) ("back flush mode"), ambient gas (purge gas) is introduced into the circulatory gas system via the flushing channel (12), and gas flows out of the circulatory gas system via the dosing channel (9). The purge gas is cleaned as it passes through the back flush filter (14). In this operating mode the direction of flow in the dosing channel (9) is reversed. The dosing channel is effectively cleaned by the filtered gas of the circulatory gas system.

The flow rate of the sample gas in "dosing mode" is determined by the pressure difference at the points where the two channels (9) and (10) join the circulatory gas system and by their flow resistances. The ratio between the flow rate of the sample gas and the flow rate in the circulatory gas system is given by the quotient of the flow resistance of the section of the circulatory gas system between the points where channel (9) and channel (10) join the circulatory gas system and the sum of their flow resistances. The mixing ratio between the sample gas and the gas in the circulatory gas system is preferably between 1:20 and 1:500, but it can also be less.

The flow rate of the purge gas in "back flush mode" is given by the pressure difference at the points where the dosing channel (9) and the flushing channel (12) join the circulatory gas system and also their flow resistances and the flow resistance of the back flush filter (14). The mixing ratio between the purge gas and the gas in the circulatory gas system is given by the quotient of the flow resistance of the circulatory gas system between the points where the channels (9) and (12) join the circulatory gas system and the sum of the flow resistances of the two channels and the back flush filter (14). As is the case in "dosing mode", the section of the circulatory gas system which is meant here is, of course, the section in the direction of the flow which lies between the respective channels. The dosing channel (9) is rapidly cleaned of accumulated substances by selecting the pipe cross-sections so that the flow rate of the purge gas is significantly higher than the flow rate of the sample gas. The mixing ratio when flushing back is less than 1:2.

The flow resistances of the channels (9), (10) and (12), and also the flow resistances of the circulatory gas system (e.g. the flow resistor (11)), can be varied manually, or preferably by electrically controlled actuators, and, depending on the type and control, either continuously or stepwise. The flow rates of the sample and purge gas can be varied in this way. Control software, for example, can switch automatically from "dosing mode" to "back flush mode" or reduce the flow rate of the sample gas when the measuring signal exceeds specified limit values. In both cases, accumulation effects are minimized and readiness for operation of the ion mobility spectrometer is increased.

The purge gas passes through the back flush filter (14) upstream of the filter (3). The back flush filter is not absolutely essential, but it provides for favorable cleaning when the aspirated gas is heavily contaminated. Filter (3), in conjunction with filter (15), isolates the gas in the measuring tube (1) from the gas pump (2). This isolation of the gas pump (2) means that a reasonably priced membrane pump with sealing elements and membrane made of an elastomer can be used, as the substances accumulated there do not reach the measuring tube (1) even when the ion mobility spectrometer is at a standstill or in storage. A further advantage of this embodiment is the damping of the pressure surges produced by the gas pump (2) in the two filters (3) and (15).

When the ion mobility spectrometer is not in operation, the channels which connect the circulatory gas system with the ambient gas are preferably sealed with a cap, a slide valve, or a twist-action, bayonet or any other type of sealing mechanism.

Figure 3:
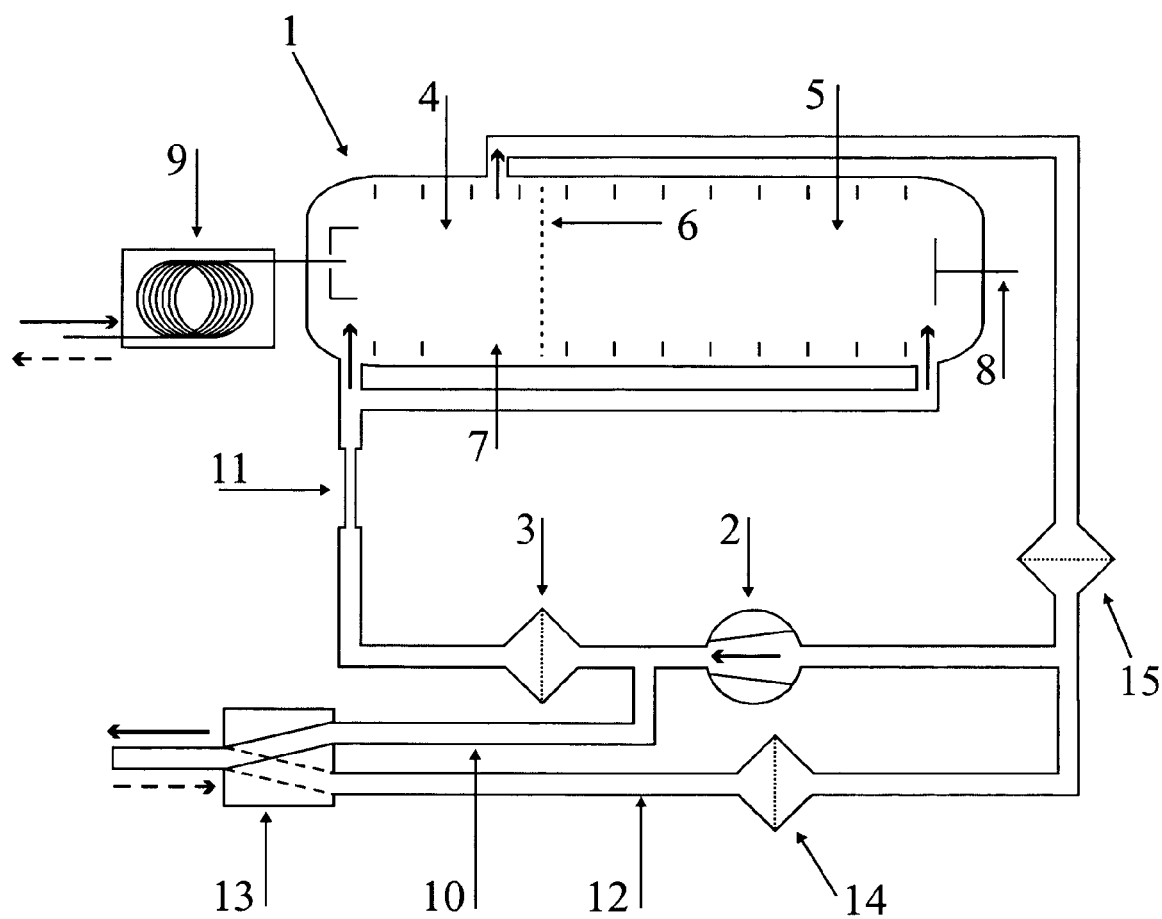
FIG. 3 shows an ion mobility spectrometer with a heatable gas chromatographic separation capillary as the dosing channel.

FIG. 3 illustrates a third preferred embodiment of an ion mobility spectrometer. This embodiment differs from the preceding one in that the dosing channel (9) is not a deactivated GC transfer capillary but rather a short GC separation capillary. In addition to the drift time in the measuring tube (1) of the ion mobility spectrometer the retention time in the GC separation capillary is acquired as additional chromatographic information. This additional dimension in the measuring signal improves the selectivity and the chances for identification of the substances to be analyzed. The substances separated in the GC separation capillary of the dosing channel (9) are introduced into the reaction chamber (4) in close proximity to the gating grid (6) and the ionization source (7) in order to facilitate a short cycle time for the analysis in the measuring tube (1). A short cycle time is necessary in this embodiment in order to preclude a temporal mixing of the substances before the analysis in the measuring tube (1).

To acquire the additional chromatographic information, the ion mobility spectrometer is initially in "back flush mode". Time series of ion mobility spectra are recorded synchronously with the switching from "back flush mode" to "dosing mode". As is known from gas chromatography, the substances to be analyzed propagate inside the GC separation capillary of the dosing channel (9) in concentration fronts at substance-dependent speeds, and consequently reach the reaction chamber (4) with different delays (retention times). This causes the characteristic measuring signals of the ion mobility spectrometer for different substances to become visible in the spectrum after different retention times and to grow at different rates. Whereas in gas chromatography a temporally pulsed sample introduction is common, in this embodiment there is a continuous sample introduction. The GC/IMS coupling produces a two-dimensional series of spectra which have the retention time in the GC separation capillary and the drift time in the drift chamber (5) as independent axes. This series of spectra can be considered as both a time series of the ion mobility spectra measured at certain points in time and a series of chromatographs for each type of ion which can be distinguished in the ion mobility spectrum. If a chromatograph of this type, which is measured with continuous sample introduction at a specific drift time in the ion mobility spectrometer, is differentiated according to the retention time axis, the chromatograph for ions with the same drift time with pulsed sample introduction is obtained.

After switching back into "back flush mode", the GC separation capillary is flushed back with cleaned gas from the circulatory gas system, and the concentration fronts propagate in the opposite direction. The propagation speed of the concentration fronts is essentially proportional to the flow rate at the same temperature. To achieve rapid cleaning of the GC separation capillary of the dosing channel (9), the flow rate of the purge gas is adjusted so as to be considerably higher than the flow rate of the sample gas. The flow rate of the purge gas is preferably around two to five times higher than the flow rate of the sample gas. In order to obtain reproducible results, the "back flush mode" is retained in practice until all the measuring signals in the ion mobility spectrum have sufficiently died away.

The flow rate of the sample gas in the preceding embodiments is around a few milliliters per minute, and hence lies in the optimum range of conventional GC separation capillaries. For some classes of substances this makes it possible to achieve a separation effect even with short GC separation capillaries only a few centimeters to a few decimeters in length. The flow resistances of this type of short GC separation capillary can be dimensioned so that the given flows are achieved even at pressure differences of a few millibars, which can easily be achieved in the ion mobility spectrometers described.

In order to characterize substances by their retention times in a GC separation capillary, the retention times must be corrected with the help of measured temperature and pressure values, or the capillary must be thermostated, or a reproducible temperature program must be run. The latter is particularly simple and effective to carry out using coated stainless steel GC separation capillaries, which are also commercially available, and which can be heated by direct current flow. The low heat capacity of this type of GC separation capillary also makes it possible to run temperature programs using relatively little energy, something which is particularly advantageous for battery-operated instruments.

Especially for low-volatility substances, a further advantageous type of operation consists in selecting the capillary coating and the initial temperature during sample introduction in such a way that the substances to be analyzed propagate at very low speed in the GC separation capillary of the dosing channel (9), and are thereby accumulated in the GC separation capillary for a few tens of seconds to a few minutes. By rapid heating of the GC separation capillary all the substance are desorbed within a few seconds and introduce into the measuring tube (1). In this "sampling mode", substances at low concentration can be enriched in the GC separation capillary, and they can only be detected in very low concentrations by this enrichment. The quickest way of cleaning the dosing channel (9) is by back flushing at a temperature above the desorption temperature. For this type of operation, too, the GC separation capillary should be in close thermal contact with an electric heater of low heat capacity, or should be heated directly, so that it can be heated rapidly and with low energy input.

A significant advantage of this embodiment compared with the GC/IMS combinations which have been usual until now is that the GC separation capillary is used directly as the dosing channel (9), requiring neither an additional valve actuation nor an additional suction pump. This makes it possible to produce a particularly compact and simple high-quality ion mobility spectrometer.

Figure 4A:
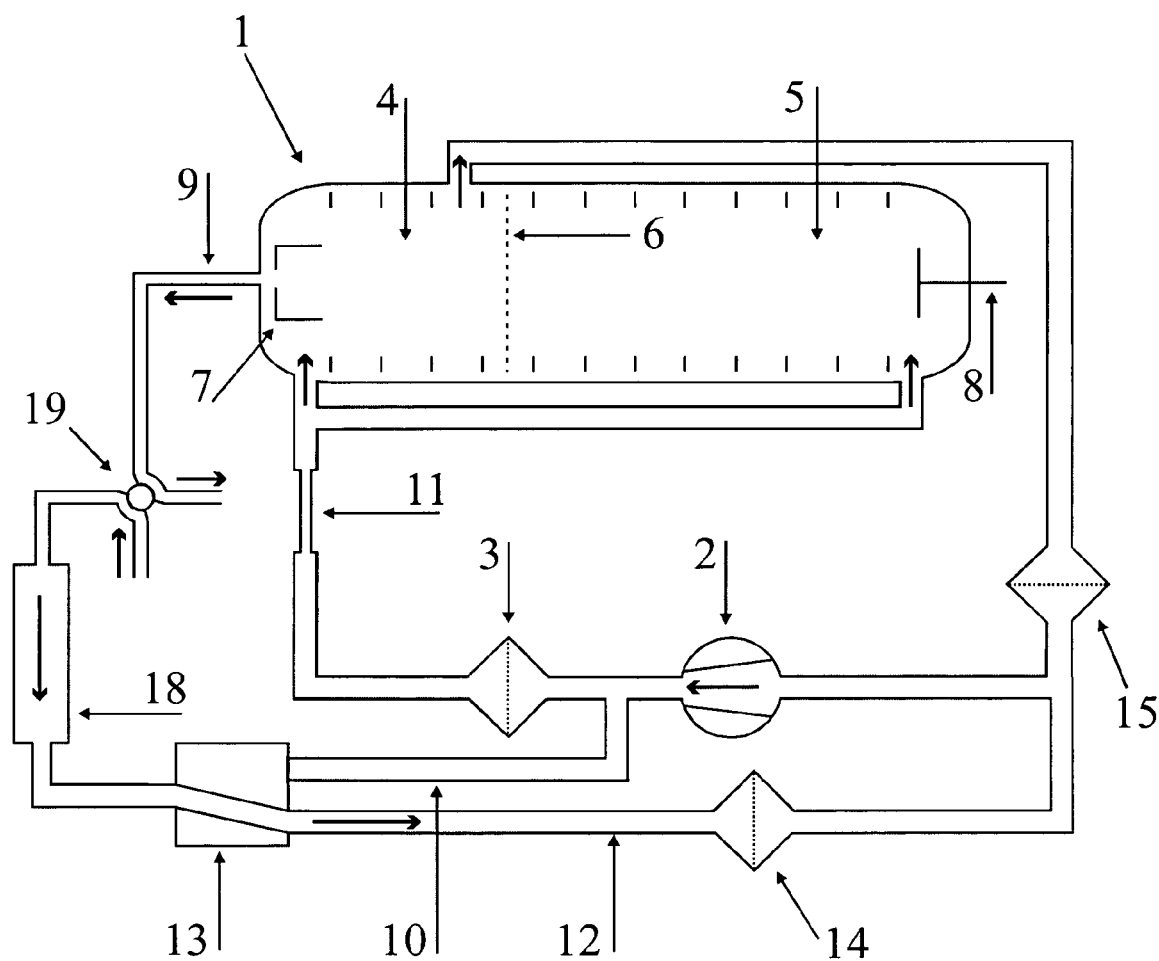
FIGS. 4a and 4b shows an ion mobility spectrometer in which a storage tube is used.
Figure 4B:
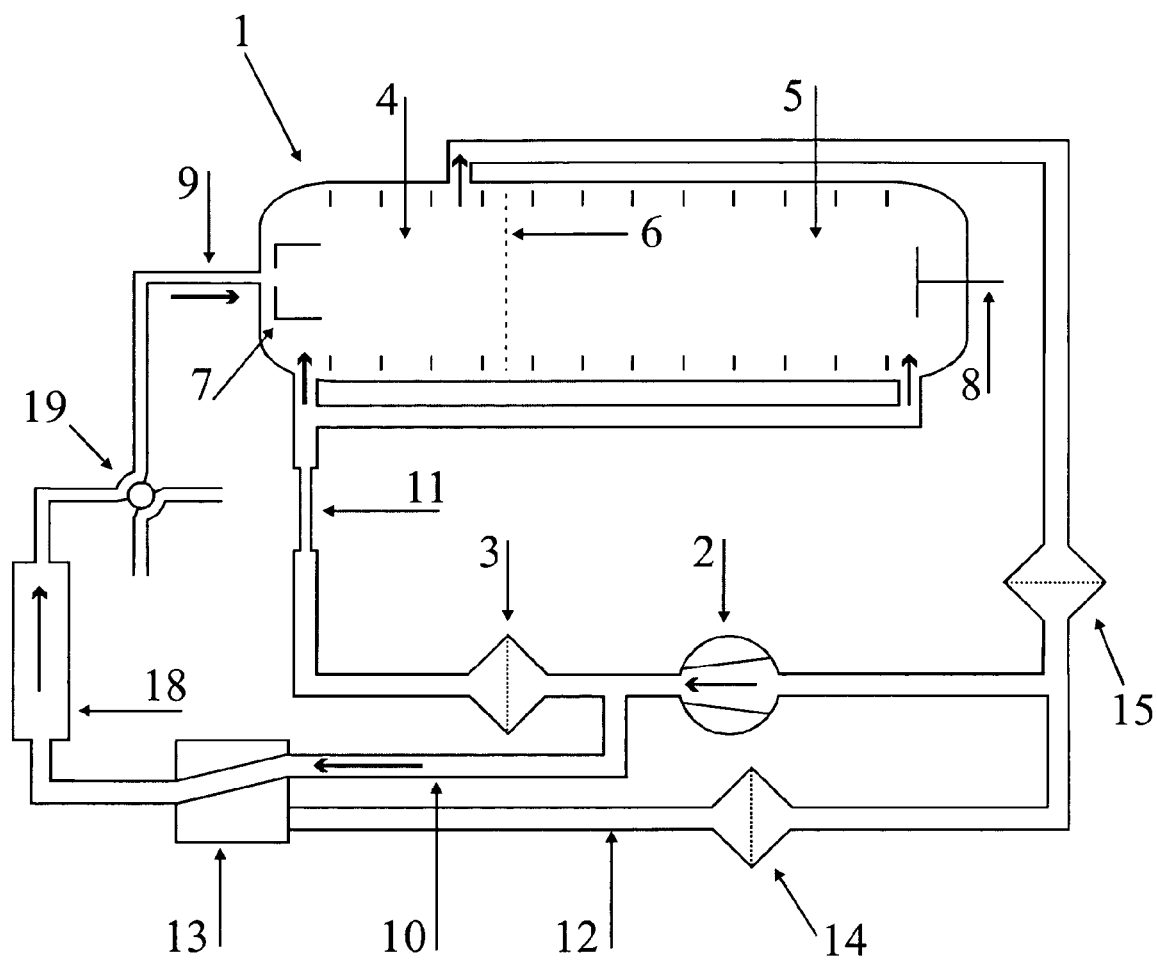

FIGS. 4a and 4b illustrate a fourth preferred embodiment of an ion mobility spectrometer. In FIG. 4a ("sampling mode"), the multi-way valve (19) and the changeover valve (13) are switched so that ambient gas is introduced into the circulatory gas system via the flushing channel (12). The ambient gas introduced first reaches the small storage tube (18) via the multi-way valve (19), and this tube stores the substances found in the ambient gas to be analyzed. The small storage tube (18) can, for example, be a Tenax adsorption tube or a capillary that is coated or contains a material on which the substances of interest are adsorbed or which dissolves them. The critical factor here is that the ambient gas to be analyzed does not pass through a filter upstream of the small storage tube (18), as otherwise quantities of the substances to be analyzed would be filtered out. Simultaneously gas flows out of the circulatory gas system via the dosing channel (9) and the multi-way valve (19).

In FIG. 4b the two valves (13) and (19) are switched so that two closed circuits are formed in "dosing mode". One part of the gas flows via the outlet channel (10) and the changeover valve (13) into the small sampling tube (18). Here, the substances to be analyzed are released again in the cleaned gas flow and introduced directly into the measuring tube (1) via the dosing channel (9). It is preferable for the small storage tube (18) to be heated at the beginning of the "dosing mode" to accelerate the release of the accumulated substances.

As in the preceding embodiments, it is advantageous here that only a single transport device is required when charging the small sampling tube (18) in "sampling mode" and introducing the sample gas in "dosing mode".

With knowledge of the invention, those skilled in the art can design a large number of other embodiments according to the invention. For example, the number of dosing channels, outlet channels and flushing channels used is not limited to one channel of each type. Furthermore, the channels which connect the circulatory gas system with the ambient gas can be opened and closed. Moreover, there can be several closed paths in the circulatory gas system, along which the gas is circulated in the circulatory gas system. Ion mobility spectrometers according to the invention are not limited to the time-of-flight type, but have the advantage that they can be used with all ion mobility spectrometers with a circulatory gas system.

What is claimed is:

1. Ion mobility spectrometer in which a measuring tube, a filter and a transport device are connected to form a circulatory gas system, with a gas inlet which introduces ambient gas for analysis to the measuring tube of the ion mobility spectrometer, wherein the measuring tube of the ion mobility spectrometer is connected with the ambient gas via a dosing channel, the circulatory gas system is connected with the ambient gas via an outlet channel, which is integrated into the circulatory gas system between a high-pressure side of the transport device and the measuring tube, the ambient gas to be analyzed is introduced into the measuring tube via the dosing channel at specified times for specified periods, and, during said specified times for specified periods, gas flows out of the circulatory gas system via the outlet channel and wherein gas flows out of the circulatory gas system via the dosing channel for a specified time when said gas is not flowing out of the outlet channel and cleans it, and there are no transport devices in either the dosing channel nor the outlet channel.

2. Ion mobility spectrometer in which a measuring tube, a filter and a transport device are connected to form a circulatory gas system, with a gas inlet which introduces ambient gas for analysis to the measuring tube of the ion mobility spectrometer, wherein the measuring tube of the ion mobility spectrometer is connected with the ambient gas via a dosing channel, the circulatory gas system is connected with the ambient gas via an outlet channel, which is integrated into the circulatory gas system between a high-pressure side of the transport device and the measuring tube, the ambient gas to be analyzed is introduced into the measuring tube via the dosing channel at specified times for specified periods, and, during said specified times for specified periods, gas flows out of the circulatory gas system via the outlet channel, wherein the flow rate of the ambient gas introduced via the dosing channel is automatically reduced if the measuring signal of the ion mobility spectrometer exceeds specified limit values, and there are no transport devices in either the dosing channel nor the outlet channel.

3. Method according to claim 2, wherein the ambient gas introduced via the dosing channel is continuously monitored for gaseous substances.

4. Ion mobility spectrometer in which a measuring tube, a filter and a transport device are connected to form a circulatory gas system, with a gas inlet which introduces ambient gas for analysis into the measuring tube of the ion mobility spectrometer, wherein the measuring tube of the ion mobility spectrometer is connected with the ambient gas via a dosing channel, the circulatory gas system is connected with the ambient gas via an outlet channel, which is integrated into the circulatory gas system between a high-pressure side of the transport device and the measuring tube, the circulatory gas system is connected with the ambient gas via a flushing channel, which is integrated into the circulatory gas system between the measuring tube and a low-pressure side of the transport device and which can be opened and closed, the ambient gas to be analyzed is introduced into the measuring tube via the dosing channel when the flushing channel is closed, and, while the flushing channel is closed gas flows out of the circulatory gas system via the outlet channel, the ambient gas is introduced into the circulatory gas system via the flushing channel when the flushing channel is open, and, while the flushing channel is opened gas flows out of the circulatory gas system via the dosing channel, which cleans the dosing channel in the process, and there are no transport devices in either the dosing channel or the outlet channel or in the flushing channel.

5. Ion mobility spectrometer according to claim 4, wherein the flow rate of the ambient gas introduced via the flushing channel is half the flow rate in the circulatory gas system or less.

6. Ion mobility spectrometer according to claim 4, wherein the ambient gas introduced via the flushing channel flows through at least one filter before entering the measuring tube.

7. Ion mobility spectrometer according to claim 4, wherein some or all of the flow resistances in the circulatory gas system can be varied either continuously or stepwise.

8. Ion mobility spectrometer according to claim 4, wherein some or all of the flow resistances of the channels connecting the measuring tube or the circulatory gas system with the ambient gas can be varied either continuously or stepwise.

9. Ion mobility spectrometer according to claim 8, wherein some or all of the channels connecting the measuring tube or the circulatory gas system with the ambient gas can be opened and closed.

10. Ion mobility spectrometer according to claim 4, wherein the flow rate of the ambient gas introduced via the dosing channel is at least twenty times smaller than the flow rate in the circulatory gas system.

11. Ion mobility spectrometer according to claim 4, wherein the flow rate of the ambient gas introduced via the dosing channel is between 1 and 20 milliliters per minute.

12. Ion mobility spectrometer according to claim 4, wherein the flow rate in the circulatory gas system is between 100 and 2000 milliliters per minute.

* * * * *